US00PP14104P39

(12) United States Plant Patent
Zary

(10) Patent No.: US PP14,104 P3
(45) Date of Patent: Aug. 26, 2003

(54) HYBRID TEA ROSE PLANT NAMED 'JACOLMAN'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/000,277

(22) Filed: Nov. 30, 2001

(65) Prior Publication Data

US 2003/0106117 P1 Jun. 5, 2003

(51) Int. Cl.[7] ..... A01H 5/00
(52) U.S. Cl. ..... Plt./139
(58) Field of Search ..... Plt./139

(56) References Cited

U.S. PATENT DOCUMENTS

PP5,519 P * 7/1985 McGredy, IV ..... Plt./139
PP6,264 P * 8/1988 Olesen et al. ..... Plt./139

OTHER PUBLICATIONS http://www.helpmefind.com/sites/rrr/pl.php?n=39724 Rose JAColman Nov. 18, 2002.*
Dean Murakami, "New Roses for 2002" in Hiptalk from the San Fernando Valley Rose Society, Inc. vol. 40, No. 6 Jun./Jul. 2001.*

* cited by examiner

*Primary Examiner*—Bruce R. Campell
*Assistant Examiner*—W C Haas
(74) *Attorney, Agent, or Firm*—Klarquist Sparkman, LLP

(57) ABSTRACT

Hybird Tea rose plant having deep red flower color; pointed ovoid bud; deep green, glossy, disease-resistant foliage; and long cutting stems.

1 Drawing Sheet

GENUS AND SPECIES

Rosa hybrida.

VARIATION DENOMINATION

'JAColman'.

SUMMARY OF THE INVENTION

The present invention relates to a new and distinct variety of rose plant of the rose class which was originated by me by crossing the variety 'MACauck' (U.S. Plant Pat. No. 5,519) with the variety 'POULman' (U.S. Plant Pat. No. 6,264).

BACKGROUND OF THE INVENTION

The primary objective of this breeding was to produce a new rose variety having red flowers with the long cutting stems of 'MACauck' combined with the deep red flower color, heavy petal substance and disease resistance of 'POULman'.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Deep red flower color;
2. Pointed ovoid bud;
3. Deep green, glossy, foliage, resistant to mildew and rust; and
4. Long cutting stems.

Asexual reproduction of this new variety by budding on Dr. Huey understock, as performed at Wasco, Calif., shows that the foregoing and all other characteristics and distinctions come true to form and are established and transmitted through succeeding propagations.

COMPARISON WITH PARENTS

Flowers of 'JAColman' are larger and of a darker red than those of 'MACauck' and 'JAColman' has a taller plant and more high-centered bud form than 'POULman'.

COMPARISON WITH SIMILAR VARIETY

'JAColman' differs from 'Red Queen' (Kordes) (unpatented), a similar variety in that 'JAColman' has a larger, more high-centered form and darker flower color.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'MACauck' (U.S. Plant Pat. No. 5,519).
*Pollen parent.*—'POULman' (U.S. Plant Pat. No. 6,264).

FLOWER

Observations made from plants of 2 years of age grown in a garden environment at Somis, Calif., January 2000–May 2001.

Blooming habit: Continuous.

Bud:

*Size.*—About 2 inches long and 3 cm in diameter when the petals start to unfurl.

*Form.*—The bud form is pointed ovoid.

*Color.*—When sepals first divide, bud color is Red Group 53B. When half blown, the upper sides of the petals are Red Group 45A; and the lower sides of the petals are Red Group 53C.

*Sepals.*—Color: Upper surface: Green Group 138B with prominent mid rib of Yellow-Green Group 145B. Lower surface: Yellow-Group 146B often with anthrocyanin coloration Greyed-Purple Group 185A. Unappendaged: Length: 35–40 mm. Width: 10–15 mm. Appendaged: Length: 45–50 mm. Width: 10–15 mm. Shape: Subulate. Surface texture: Covered in fine hairs. There are three heavily appendaged sepals. There are two unappendaged sepals with hairy edges.

*Receptacle.*—Color: Yellow-Green Group 146C often with Greyed-Purple Group 183C anthocyanin present when expoed to bright sunlight. Shape: Funnel. Size: Large, about 12 mm×9 mm. Surface: Smooth.

*Peduncle.*—Length: Medium, averaging about 85–95 mm. Surface: Smooth, with a few glands. Color: Yellow-Green Group 146C often with pronounced anthrocyanin, Greyed-Purple Group 184A. Strength: Stiff, erect, heavy.

Bloom:

*Size.*—Large. Average open size is about 13 cm.

*Borne.*—Singly.

*Stems.*—Strength: Strong. Average length is about 55–65 cm.

*Form.*—When first open: high centered. Permanence: Retains its form to the end. Outer petal edges curl slightly with moderate quilling.

*Petalage.*—Number of petals under normal conditions: 35.

*Color.*—The upper sides of the petals are Red Group 45A. The reverse sides of the petals are Red Group 53C. The base of each petal has a small 4 mm×4 mm color spot of Yellow Group 8D. The major color on the upper side is Red Group 45A.

*Variegations.*—Occassional variegation on guard petal midrib of Yellow Group 4D.

*Discoloration.*—The general tonality at the end of the first day: No change. At the end of the third day: No change. By day seven on the plant, the major color changes to Red Group 53C. By day nine on the plant, the petals fall.

*Fragrance.*—Slight.

Petals:

*Texture.*—Thick, leathery.

*Shape.*—Round to slightly deltoid.

*Margin.*—Entire.

*Apex shape.*—Obovate.

*Base shape.*—Lanceolate.

*Form.*—Tips slightly recurved, edges slightly quilled.

*Arrangement.*—Imbricated.

*Petaloids in the center.*—None to three per bloom. Color: Red Group 53D. Length: 7–10 mm. Width: 3–8 mm.

*Persistence.*—Petals drop off cleanly before drying.

*Lastingness.*—On the plant: Long (about 8–9 days). As a cut flower: Long (about 10–11 days).

Reproductive parts:

*Stamens.*—Number: 90–120. Anthers: Size: Large. Length: 10–12 mm. Color: Orange-White Group 159A. Filaments: Color: Greyed-Purple Group 185D. Pollen: Color: Yellow-Orange Group 22C.

*Pistils.*—Number: 90–100. Length: 5–8 mm. Styles: Color: White-Yellow Group 158D with anthrocyanin pigment of Red-Purple Group 65C. Length: 7–13 mm. Stigmas: Color: Orange-White Group 159A. Length: 1–2 mm.

*Hips.*—None observed.

Plant:

*Form.*—Bush.

*Growth.*—Very vigorous, upright and branching.

*Mature plant.*—Height: 6 feet. Width: 4 feet.

Foliage: Number of leaflets on normal mid-stem leaves: 5 or 7.

*Size.*—Large (6–7 inches long×4–5 inches wide).

*Quantity.*—Abundant.

*Color.*—New foliage: Upper and lower sides: Greyed-Purple Group 183A. Old foliage: Upper side: Green Group 137A. Lower side: Yellow-Green Group 147B.

Leaflets:

*Size.*—Length: 50–76 mm. Width: 25–50mm.

*Shape.*—Ovate.

*Tip shape.*—Obtuse.

*Apex shape.*—Acute.

*Texture.*—Leathery.

*Edge.*—Serrated.

*Serrations.*—Single and small.

*Petiole color.*—Yellow-Green Group 146D.

*Petiole rachis.*—Color: Yellow Group 146B with Greyed-Purple Group 184C antrocyanin.

*Petiole underside.*—Smooth with only an occassional prickle; Color: Yellow Group 146D.

*Stipules.*—Medium, serrated (about 12–14 mm. in length, 4–5 mm in width).

*Disease resistance.*—Resistant to mildew and rust; susceptible to blackspot under normal growing conditions.

*Pest resistance.*—Not observed.

Wood:

*New wood.*—Color: Greyed-Purple Group 184A. Bark: Smooth.

*Old wood.*—Color: Yellow-Green Group 147A. Bark: Smooth.

Prickles:

*Quantity.*—On main canes from base: Ordinary (11–15 per 15 cm of stem). On laterals from main canes: Ordinary (11–15 per 15 cm of stem).

*Form.*—Medium, hooked slightly downward.

*Color when young.*—Greyed-Purple Group 185A.

*Color when mature.*—Greyed-Orange Group 164D.

Small prickles:

*Quantity.*—On main stalks: None on main stalks. On laterals: None on main laterals.

Winter hardiness: Hardy to Zone 5.

I claim:

1. A new and distinct variety of rose plant of the hybrid class, substantially as herein shown and described, characterized particularly by deep red flower color; pointed ovoid bud; deep green, glossy, disease-resistant foliage; and long cutting stems.

* * * * *

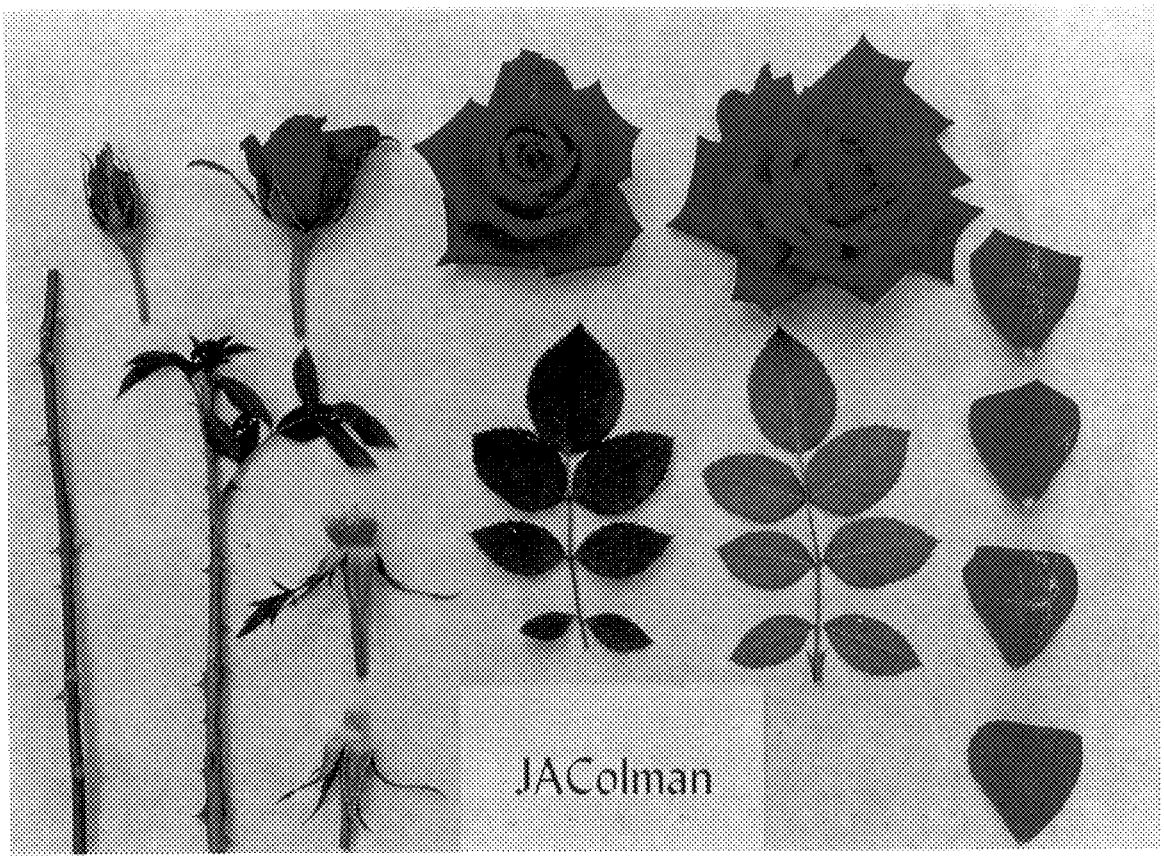
JAColman